United States Patent [19]

Iwama et al.

[11] 4,102,807

[45] Jul. 25, 1978

[54] HYDROUS GEL AND PROCESS FOR ITS PREPARATION

[75] Inventors: Akio Iwama; Isao Mune, both of Ibaraki, Japan

[73] Assignee: Nitto Electric Industrial Co., Ltd., Ibaraki, Japan

[21] Appl. No.: 679,611

[22] Filed: Apr. 23, 1976

[30] Foreign Application Priority Data

Apr. 24, 1975 [JP] Japan .................................. 50-50300

[51] Int. Cl.² ............................................. B01J 13/00
[52] U.S. Cl. .................................... 252/316; 252/309; 260/29.7 UA
[58] Field of Search ............................... 252/316, 309; 260/29.6 UA, 29.6 PM, 29.6 WQ

[56] References Cited

U.S. PATENT DOCUMENTS

| | | | |
|---|---|---|---|
| 3,442,842 | 5/1969 | Bonin | 252/309 |
| 3,489,690 | 1/1970 | Lachampt et al. | 252/309 |
| 3,740,421 | 6/1973 | Schmolka | 252/316 |
| 3,879,575 | 4/1975 | Dobbin | 252/316 |

*Primary Examiner*—Benjamin R. Padgett
*Assistant Examiner*—Josephine Lloyd
*Attorney, Agent, or Firm*—Sughrue, Rothwell, Mion, Zinn and Macpeak

[57] ABSTRACT

A hydrous gel consisting essentially of a heat-moldable w/o emulsion comprising about 15 to about 95% by weight of a continuous phase of an A-B-A type teleblock copolymeric elastomer and an oil component and about 85 to about 5% by weight of an emulsified dispersed water phase. The hydrous gel is prepared by dissolving the teleblock copolymeric elastomer in an excess of the oil component by heating, adding an emulsifier and water to the solution to disperse the water therein and to form the w/o emulsion, and then cooling the resulting emulsion to room temperature. The hydrous gel finds a wide range of utility, for example, as an insulator, especially to maintain low or high temperature environments, as a fireproofing material, as a heat absorbant, and as a hospital mat.

22 Claims, 2 Drawing Figures

HYDROUS GEL AND PROCESS FOR ITS PREPARATION

BACKGROUND OF THE INVENTION

1. Field of the Invention

This invention relates to a hydrous gel of a novel structural form comprising a continuous phase composed of a certain elastomer and an oil component and an emulsified water phase, and a process for its preparation, and more specifically, is characterized in that as a result of the presence of the emulsified water phase in the form of a w/o emulsion in the gel structure, the hydrous gel has unique physical, mechanical and chemical properties as compared with conventional aqueous gels or oily gels.

2. Description of the Prior Art

Relatively sort aqueous gels comprising various water soluble organic polymeric compounds, such as starch, cellulose derivatives, gelatin, casein, polyvinyl alcohol, polyvinyl pyrrolidone, polyacrylic acid, or polyethylene oxide, are known, and find applications as fire-retarding materials and insulating (heat and cold retention) materials, etc. Most of these aqueous gels, however, are of such a form that they are swollen as a result of the absorption of water by the water soluble polymers. Hence, in most of these aqueous gels water forms a continuous phase. For this reason, when the water content is relatively high, the strength of the aqueous gel is not so high, and generally, it has poor storage stability. When such aqueous gels are allowed to stand in the air, water present therein evaporates off easily. Furthermore, when such aqueous gels are utilized as a cold-retaining material and are stored at a temperature below 0° C, they suffer from the defect that the entire gel freezes and becomes very hard and brittle, thus losing its softness.

Japanese Patent Publication 18,409/72 discloses the preparation of a highly elastic gel composed of an elastomeric block copolymer and a certain oil or a higher fatty acid as an oily gel which, in particular, has good softness and high elasticity. The oily gel disclosed, however, has a rubber like high impact resilience and easily deforms upon the application of stress but returns to its original state upon removal of the stress. Accordingly, it has very poor stress dispersing characteristics as will later be described. Furthermore, since this oily gel is combustible, it is unsuitable for use as a fireproofing material, and because it does not contain a water phase, it has practically no insulating (cold retention) effect.

SUMMARY OF THE INVENTION

Accordingly, it is one object of this invention to provide a hydrous gel of a novel structural from which can be molded by heat and which consists essentially of a w/o emulsion comprising a continuous phase of a certain elastomer and an oil component and an emulsified water dispersed phase.

Another object of this invention is to provide a gel product which has marked stress dispersing characteristics as a result of the presence of a dispersed phase of emulsified spherical water particles in the gel structure, that is, a gel product which easily deforms upon the application of stress but completely returns to its original state in about 1 to 2 minutes after the removal of stress, which can be used, for example, as a gel mat to prevent the congestion of blood in a seriously wounded patient who cannot move his body, particularly at his hips, during prolonged hospitalization.

Still another object of this invention is to provide a hydrous gel of high utility characterized by its excellent insulating capability (cold and heat retention capability), self-extinguishing properties, sound absorbing properties, etc., which is substantially stable when the water content in the gel structure is up to about 85% by weight, and which does not lose softness even at −20° C.

DETAILED DESCRIPTION OF PREFERRED EMBODIMENTS

Figure 1:
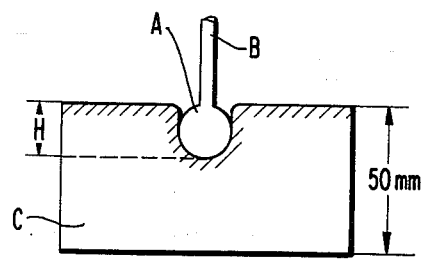
FIG. 1 shows a device for measuring the stress dispersing characteristics of the gel particles of the present invention.

According to the present invention, there is first provided a hydrous gel consisting essentially of a heat-moldable w/o emulsion comprising about 15 to about 95% by weight of a continuous phase containing an A-B-A teleblock copolymeric elastomer and an oil component and about 85 to about 5% by weight of a dispersed water phase resulting from the emulsification of water particles by an emulsifier, the hydrous gel providing a gel product containing emulsified water particles which are stable at room temperature.

According to another aspect of this invention, there is provided a process for preparing a hydrous gel, which comprises dissolving an A-B-A teleblock copolymeric elastomer in a large amount (more than 3 times by weight of the elastomer) of an oil component by heating, adding an emulsifier and water to the resulting solution to disperse water therein and to form a w/o emulsion comprising about 15 to about 95% by weight of a continuous phase containing the elastomer and the oil component and about 85 to about 5% by weight of an emulsified dispersed water phase, and then cooling the emulsion to room temperature.

The A-B-A teleblock copolymeric elastomer (hereafter referred to as a teleblock elastomer) used to form the continuous phase contains a hard polymer block A and a soft polymer block B. The block A is a hard polymer of a vinyl compound. Suitable polymers are those having a glass transition point of at least about 70° C and an average molecular weight of about 1,000 to about 100,000. The block B is a soft polymer of a conjugated diene compound. Suitable polymers are those having a glass transition point of about −50° C to about 30° C and an average molecular weight of about 4,500 to about 1,000,000.

Examples of vinyl compounds include monovinyl aromatic compounds having 8 to 20, more preferably 8 to 12, carbon atoms per molecule and a glass transition point of at least about 70° C and an average molecular weight of about 1,000 to about 100,000. Representative examples of such are styrene, saturated alkyl styrene derivatives, e.g., methylstyrenes such as 3-methylstyrene, 3,5-dimethylstyrene, or the like, 3-ethylstyrene, 4-propylstyrene, 2,4,6-triethylstyrene, vinylnaphthalenes such as 1-vinylnapthalene, 2-vinylnaphthalene etc. Acrylic acid or methacrylic acid derivatives, e.g., acrylonitrile, methacrylonitrile, methyl methacrylate, methyl acrylate, α-methylstyrene, etc., can also be employed.

Examples of diene compounds include conjugated dienes having 4 to 12, more preferably 4 to 8, carbon atoms per molecule and a glass transition point of about −50° C to about 30° C and an average molecular weight of about 4,500 to about 1,000,000. Specific examples of diene compounds are isoprene, butadienes such as 1,3-butadiene and 2,3-dimethyl-1,3-butadiene, 1,3-pentadiene, 3-methyl-1,3-pentadiene, 2-methyl-3-ethyl-1,3-butadiene, 1,3-hexadiene, 1,3-heptadiene, 3-butyl-11,3-octadiene, 2-phenyl-1,3-butadiene, 2-methyl-3-isopropyl-1,3-butadiene, etc.

The terminal blocks A account for about 15 to about 65% by weight of the entire teleblock elastomer, the balance being the blocks B.

The oil component, another component of the continuous phase, is an oily substance which is liquid at room temperature and is miscible with the block B of the teleblock elastomer but immiscible with the block A. Examples of oil components include liquid paraffins, paraffin base oil, naphthenic base oil and mixtures of these components, e.g., commercially available oils such as a mixture of paraffin base oil and naphthenic base oil such as machine oils, cylinder oils, transformer oils and the like, having a density of about 0.83 to about 0.89, and a viscosity of about 9.0 to about 200 cSt (at 37.8° C). Rosin oils can also be used. Mixtures of these oily substances with a substance which becomes oily upon heating, such as a paraffin wax having a melting point of not more than about 120° C or a low molecular weight waxy polyethylene having a melting point of not more than 150° C, are also useful as the oil component in this invention. Usually, the substance which becomes oily upon heating is used in a proportion of no more than about 20% by weight of such a system.

The amount of the oil component effective for forming the continuous phase of the hydrous gel is 100 parts by weight per about 5 to about 30 parts by weight of the teleblock elastomer. The amount of the teleblock elastomer is determined mainly according to the relation between the water content of the final hydrous gel product and the desired softness. Generally, an increased amount of elastomer gives rise to an increased elasticity of the final hydrous gel product and an increased amount of water leads to an increased softness of the product.

In order to increase the toughness of the final hydrous gel of this invention, a cross-linking agent for the teleblock elastomer may be used in combination therewith. Useful cross-linking agents are curing agents and curing promotors which are usually employed for the vulcanization of rubbers. Examples of useful cross-linking agents are sulfur, tetramethylthiuram disulfide, tetramethylthiuram monosulfide, dipentamethylenethiuram tetrasulfide, zinc dimethyldithiocarbamate, zinc diethyldithiocarbamate, zinc oxide, zinc stearate, methylethyl ketone peroxide, cumene hydroperoxide, dicumyl peroxide, lauroyl peroxide, benzoyl peroxide, etc. A suitable amount of the cross-linking agent is about 0.01 to about 2 parts by weight per 100 parts by weight of the teleblock elastomer. The optimum amount is determined according to the relation of the toughness of the final hydrous gel to its softness.

Furthermore, if desired, an antioxidant may be added to the teleblock elastomer or oil component in an amount of about 0.01 to about 2 parts by weight to 100 parts by weight of the elastomer in order to prevent the deterioration of the gel by heat, oxidation, light, etc., and a reinforcing filler, coloring pigment or dye may be also added to the teleblock elastomer or oil component.

The emulsifier used in this invention should have the property of forming a dispersed phase of innumerable emulsified water particles in the above continuous phase consisting of the teleblock elastomer and the oil component and maintain the form of the w/o emulsion in a stable fashion. While not to be construed as limitative, the emulsified water particles preferably have a mean particle size of about 0.1 to about 20 $\mu$, more preferably from about 0.1 to about 7 $\mu$. Nonionic surface active agents are especially effective as this type of emulsifier. Specific examples include polyethylene glycol monooleyl ether, polyethylene glycol monononyl phenyl ether, polyethylene glycol monododecyl phenyl ether, polyethylene glycol monolauryl ether, sorbitan monolaurate, sorbitan monooleate, sorbitan sesquioleate, sorbitan monostearate, sorbitan monopalmitate, etc. Suitable commercial grades of such nonionic surface active agents are, for example, NOIGEN EA-50, -70, -80, -33, -73, -83, NOIGEN ET-60, -80, -83, and SORGEN-30, -40, -50, -70, -90, products of Daiichi Kogyo Seiyaku Co., Ltd.

The water emulsified using the above emulsifier may be pure water or may contain ions such as certain metallic ions or halogen ions, e.g., city water or natural water. The water may also contain water soluble organic materials such as perfumes, dyes or colors, or inorganic materials such as calcium carbonate or sodium carbonate in amounts which do not adversely affect the emulsification of the water or the stability of the final hydrous gel in order to color the hydrous gel or improve its fire retardancy or for other purposes. The amount of the emulsifier for emulsifying various kinds of water varies according to the amount and type of the water to be contained in the final hydrous gel, but is generally about 1 to about 20 parts by weight, preferably 5 to about 10 parts by weight, per 100 parts by weight of water.

The teleblock elastomer used in this invention can be obtained in accordance with the method disclosed in Japanese Patent Publication 19,286/1961 or Japanese Patent Publication 24,915/1965.

One preferred way of preparing the hydrous gel of this invention comprises dissolving the teleblock elastomer and the desired additives in a large amount of the oil component by heating, adding the nonionic surface active agent as an emulsifier to the resulting solution and adding water dropwise thereto to emulsify the water and form a w/o emulsion. The time for adding the water varies widely according to the compounding proportions of the respective components and the rate or speed of stirring. For example, when the speed of stirring is raised, water can be added not dropwise but continuously at a definite flow rate. This results in the formation of a stable heterogeneous system in which the continuous phase is a solution of the elastomer in the oil component and the dispersed phase consists of emulsified water particles. By cooling the heterogeneous system to a temperature within the room temperature range to gel the continuous phase, a hydrous gel is obtained which envelops the water in the form of emulsified particles.

In this example of preparation, a mixture in predetermined proportions of the teleblock elastomer and the oil component is dissolved by heating it to a temperature of about 80° to about 170° C. The resulting solution is a flowable material having a viscosity of about 10 to about 500 poises at a temperature of about 80° C or above. With decreasing temperature, the viscosity of this material rises abruptly, and at a temperature of 50° C to room temperature, it becomes a non-flowable oily gel. The emulsification of water in the solution is performed at atmospheric pressure and a temperature of about 80°0 to about 100° C. It can be carried out at a temperature of about 100° to about 130° C at elevated pressure, for example, in an autoclave. After adding the emulsifier, water is added dropwise to form a w/o emulsion.

In the present invention, each of the steps of the above example of preparation can be somewhat modified or replaced. For example, when a thermally stable emulsifier is used in the emulsifier addition step, it can be added in advance to the mixture of the teleblock elastomer and the oil component. Alternatively, a solution of dispersion of the emulsifier in water can be added to the solution prepared from the teleblock elastomer and the oil component by heating. The amount of water that can be emulsified can vary from an extremely small amount to about 85% by weight as the water content of the final hydrous gel. When water is added in a greater amount, e.g., the water content is above about 90% by weight, the stability of the hydrous gel becomes poor, or the w/o emulsion is converted to an o/w emulsion, thus preventing gelation.

Accordingly, the hydrous gel of this invention envelops water particles substantially stably in the emulsified water dispersed phase in a proportion of about 85 to about 5% by weight, and the proportion of the continuous phase consisting of the teleblock elastomer and the oil component (elastomer: oil component = about 5 to about 30 parts by weight: 100 parts by weight) is limited to about 15 to about 95% by weight based on the total weight of the product.

The hydrous gel of this invention is available in various forms. For example, the resulting w/o emulsion, if desired, after adding a vulcanizing agent, for example, can be cast into a mold, extruded, or coated on the surfaces of a material such as a fabric, paper or mold releasing paper using a coating apparatus, while being maintained flowable at a temperature of about 70° to 90° C. Subsequent cooling to a temperature within the room temperature range provides hydrous gel products in various forms. The rate of cooling has substantially no effect on the particle size and stability of the emulsion. The term "room temperature range" herein indicates the temperature range where the hydrous gel of this invention can be obtained and is generally below about 35° C.

The hydrous gel of this invention comprises a w/o emulsion structure, and water in the gel is very stable. Even when the gel is allowed to stand at room temperature for long periods of time, the loss of water is very small. Almost no loss of water is observed with products obtained by covering the hydrous gel with a plastic film.

Depending upon the types and amounts of the teleblock elastomer and the oil component, the water content, etc., the hydrous gel of this invention can exist in various forms ranging from a very soft gel to a relatively tough gel. The hydrous gel possesses excellent properties. For example, it has excellent stress dispersing characteristics and can gradually return to the original form from stress deformation. Also, it has good insulating properties, especially cold retention properties, and good self-extinguishing properties. Because of these properties, the hydrous gel of this invention can be used in various applications, for example, as a hospital mat for sick persons, as an insulator (cold and heat retention material), as a fireproofing material, as a heat absorbing material, and as a lubricating material, and its utilitarian value is very high.

As will be obvious to one skilled in the art, hydrous gels which gradually release water, perfumes, etc., contained therein over a long period of time can be obtained by selecting suitable proportions of the continuous phase and the dispersed phase in the gel. The Examples illustrate this effect.

The following Examples and Comparative Examples illustrate the present invention more specifically. It is to be noted, however, that these Examples do not in any way limit the present invention. All parts in these Examples are by weight.

EXAMPLE 1

A 1 l three-necked flask equipped with a stirrer of good efficiency, a reflux condenser and an opening for nitrogen gas introduction was charged with 100 parts of a machine oil (paraffin-naphthene) having a specific density of 0.880 and a viscosity of 330 centipoises (at 20° C) (145 CST at 37.8° C) (Daphne mechanic oil-Mechanic 75, trademark for a product of Idemitsu Kosan Co., Ltd.) and 10 parts of a styrene/butadiene/styrene teleblock elastomer (styrene (block A)/butadiene (block B) = 30/70 wt%) having an intrinsic viscosity of 1.00 and a 300% modulus of 400 psi (ASTM method D412—tensile tester jaw separation speed: 10 in/min) (Kaliflex TR-1101, trademark for a product of Shell Chemical Co.), and with stirring under an atmosphere of nitrogen gas they were heated to about 130° C to form a solution. To the resulting solution there was added 5 parts of a nonionic emulsifier consisting of polyethylene glycol monononylphenyl ether (NOIGEN EA-50, trademark for a product of Daiichi Kogyo Seiyaku Co., Ltd.) which dissolved therein. Then, while maintaining the temperature of the interior of the flask at about 80° to 90° C, 100 parts of distilled water was gradually added dropwise over the course of about 2 hours with thorough stirring. A w/o emulsion was formed.

The resulting white emulsion was heated to about 80° C to render it flowable, and cast into a mold of a depth of 50 mm. It was then cooled to a temperature within the room temperature range to form a soft hydrous gel having a volume of 100 × 100 × 55 mm.

When this hydous gel was subjected to a water resistance test by being allowed to stand in water for 12 hours at room temperature (20° C), it did not show any appreciable deformation. When it was allowed to stand for 20 days at room temperature (20° C) in the atmosphere, its weight loss was only 1.7%.

The stress dispersing characteristics of this hydrous gel were measured by means of a transmission type stress measuring instrument, a rheometer (Model RUD-J, a product of Fuji Rika Kogyo K.K.). The measuring methods will be described with reference to FIG. 1 of the accompanying drawings which shows a device for measuring the stress dispersing characteristics of gel products of the present invention and of comparison gel products. A rod (B) with a steel ball (A) having a diameter of 18 mm and a weight of 34.5 g is interlocked with the main body of a rheometer (not shown). The steel ball (A) is caused to gradually sink into the gel (C), and the relationship between the penetration distance (H) of the steel ball and the stress exerted on the rod (B) is measured.

When the penetration distance was 30 mm and the steel ball was buried in the gel, the repulsive stress exerted on the rod (B) was as low as about 300 g. When the steel ball was removed, the gel completely returned to its original form in about 1.5 minutes.

The above properties show that the hydrous gel of this invention is soft and tough, and has superior stress dispersing characteristics. The stress dispersing characteristics seem to be ascribable to the fact that the water particles in the gel deform easily upon the application of external force and exhibit the function of absorbing or dispersing the external force.

A gel mat prepared to utilize these properties of the hydrous gel of this invention is effective to prevent bed sores, for example, it prevents blood congestion in a patient's hip which might be caused by prolonged hospitalization.

COMPARATIVE EXAMPLE 1

A 1 l beaker was charged with 100 parts of the same machine oil as used in Example 1 (Daphne mechanic oil-Mechanic 75, trademark for a product of Idemitsu Kosan Co., Ltd.) and 10 parts of the same styrene/butadiene/styrene teleblock elastomer as employed in Example 1 (Kaliflex TR-1101, trademark for a product of Shell Chemical Co.), and they were heated to about 130° C to form a solution. The solution was cast into the same mold as was used in Example 1, and then cooled to form an oily gel having a volume of 100 × 100 × 50 mm.

The stress dispersing characteristics of this oily gel was measured in the same manner as in Example 1. It was found that the stress exerted on the portion (B) at a steel ball penetration distance of 30 mm was about 1,800 g, which is a very high impact resilience. When the steel ball was removed from the gel, the gel instantaneously returned to the original form, thus showing the characteristics of a highly elastic gel. When a flame was brought close to this oily gel, the gel immediately burned. Furthermore, the comparison oily gel at −10° C formed to have a volume of 100 × 200 × 10 mm possessed no substantial cold retention capability, as shown by line 1 of FIG. 2 of the accompanying drawings, which is a diagram illustrating the cold retention capability of the hydrous gels of this invention and comparison gels.

EXAMPLE 2

The same flask as was used in Example 1 was charged with 100 parts of a cylinder oil (paraffin-naphthene) having a specific density of 0.8763 and an intrinsic viscosity of 240 centipoises (at 20° C) (107 CST at 37.8° C) (MC-500, trademark for a product of Idemitsu Kosan Co., Ltd.) and 20 parts of a styrene/isoprene/styrene teleblock elastomer (styrene (block A)/isoprene (block B) = 14/86 wt%) having an intrinsic visocity of 1.13 and a 300% modulus of 100 psi (test method is the same as in Example 1) (Kaliflex TR-1107, trademark for a product of Shell Chemical Co.), and, with stirring under a nitrogen gas atmosphere, they were heated to about 140° C to form a solution. To the resulting solution there was added 10 parts of a nonionic emulsifier consisting of polyethylene glycol monooleyl ether (NOIGEN ET-80, trademark for a product of Daiichi Kogyo Seiyaku Co., Ltd.), and, in the same way as in Example 1, 300 parts of deionized water was added and emulsified to form a w/o emulsion. The resulting white emulsion was heated to about 80° C to render it flowable, and cast into a mold. It was then cooled to form a hydrous gel having a volume of 300 × 300 × 50 mm.

A steel ball having a diameter of 100 mm and a weight of 5 kg was placed on the resulting hydrous gel, and allowed to remain thereon for 48 hours to deform the hydrous gel. When the steel ball was removed, the hydrous gel returned to its original form in about 2 minutes, and no misshaping was observed.

When the hydrous gel was allowed to stand for 8 hours in a refrigerated chamber held at −10° C and then taken out into the atmosphere and held at room temperature (20° C), it had such softness that it could be deformed by the touch of a finger tip. On the other hand, a period of about 8 hours was required until the entire hydrous gel attained a temperature of 20° C after withdrawal from the refrigerated chamber. This hydrous gel is useful as a cold retention (insulating) material which utilizes the high heat capacity of the water enveloped in the gel.

EXAMPLE 3

To a solution (about 90° C) consisting of 100 parts of liquid paraffin having a specific density of 0.855 and a viscosity of 170 centipoises (at 20° C) (76 CST at 37.8° C) (first reagent grade, a product of Wako Junyaku K.K.) and 15 parts of Kaliflex TR-1107 (trademark for a product of Shell Chemical Co.) there was added 10 parts of a nonionic emulsifier consisting of polyethylene glycol monododecylphenyl ether (NOIGEN EA-73, trademark for a product of Daiichi Kogyo Seiyaku Co., Ltd.). In the same way as in Example 1, 250 parts of city water was added thereto and the system emulsified to form a w/o emulsion. The emulsion was then heated to about 80° C, cast into a mold and cooled to room temperature (20° C) to form a hydrous gel pad having a volume of 100 × 200 × 10 mm.

When this gel pad was subjected to a water resistance test by allowing it to stand in water for 12 hours at room temperature (20° C), no deformation was observed. When it was allowed to stand for 20 days at room temperature (20° C) in the atmosphere, its weight loss was 2.4%.

This gel pad was useful as a cold retention pad (insulator). When the gel pad was allowed to stand for 24 hours in a refrigerated chamber at −10° C, it retained sufficient softness so that it could be wound around the wrist or helically wrapped up.

Figure 2:
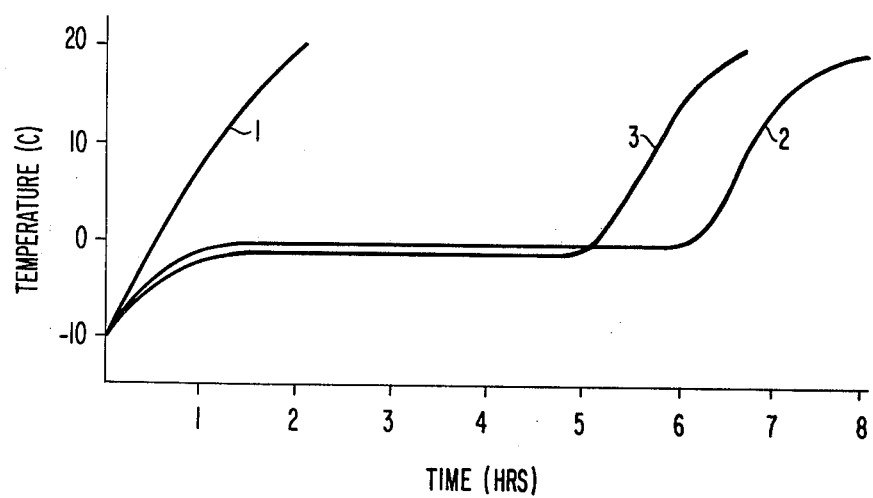
FIG. 2 is a plot illustrating the cold retention capability of various samples produced in the Examples.

The time required until the entire gel pad attained room temperature (20° C) after withdrawl from the refrigerated chamber at −10° C into the atmosphere at room temperature is shown by line 2 of FIG. 2. The pad showed excellent cold retention capability.

COMPARATIVE EXAMPLE 2

A mixture composed of 5 parts of carboxymethyl cellulose containing about 4.5 mol% carboxymethyl groups and 95 parts of city water was well stirred while being heated at about 70° C to form a gel-like solution. The solution was cast into a mold, and cooled to form an aqueous gel pad having a volume of 100 × 200 × 10 mm.

When subjected to the same water resistance test as in Example 3, this aqueous gel pad swelled and deformed markedly. When it was allowed to stand at room temperature for 20 days in the atmosphere, its weight loss was 29%.

When this gel pad was allowed to stand for 24 hours in a refrigerated chamber at −10° C, it became an ice-like frozen material totally lacking softness, and could not be wound up around the wrist, for example. The time required until the entire gel pad attained room temperature after withdrawal from the refrigerated chamber as in Example 3 is shown by line 3 of FIG. 2.

EXAMPLE 4

To a solution (about 90° C) consisting of 60 parts of liquid paraffin (the same as described in Example 3), 40 parts of low molecular weight polyethylene having an average molecular weight of about 2,000 and a softening point of about 107° C (SANWAX 151-P, trademark for a product of Sanyo Chemical Industries, Ltd.) and 20 parts of a styrene/butadiene/stryene teleblock elastomer (styrene (block A)/butadiene (block B) = 40/60 wt%) having an intrinsic viscosity of 1.50 and a 300% modulus of 400 psi (test method is the same as in Example 1) (Solprene-411, trademark for a product of Asahi Chemical Industry Co., Ltd.) there was added 7 parts of a nonionic emulsifier (NOIGEN EA-83, trademark for a product of Daiichi Kogyo Seiyaku Co., Ltd.). In the same way as in Example 1, 100 parts of a 25% aqueous solution of sodium carbonate was added thereto and the system emulsified to form a w/o emulsion.

The emulsion was coated on a silicone resin coated mold release paper at a temperature of about 90° C in the form of a 2 mm thick sheet, and cooled to room temperature to form a hydrous gel. The resulting gel had self-extinguishing properties. It only slightly burned while in contact with a flame, but upon removal of the flame it self-extinguished.

Furthermore, this hydrous gel sheet had tackiness, whereby it could be firmly adhered to glass, wood and paper. For example, the surface of crepe paper could be directly covered with this hydrous sheet. When a lighted cigarette was placed on this laminate, the flame of the cigarette was extinguished by the hydrous gel layer, and no burning of the paper was observed. Thus, a further use of such a hydrous gel sheet is as a fireproofing sheet.

EXAMPLE 5

A solution was prepared in the same way as in Example 1 by heating 100 parts of liquid paraffin having a specific density of 0.887 and viscosity of 400 centipoises (20° C) (175 CST at 37.8° C) (Kyoseki Liquid Paraffin-350, trademark for a product of Kyodo Sekiyu K.K.) and 10 parts of Kaliflex TR-1107 (trademark for a product of Shell Chemical Co.). To the resulting solution was added 5 parts of a nonionic emulsifier consisting of sorbitan monostearate (SORGEN-50, trademark for a product of Daiichi Kogyo Seiyaku Co., Ltd.). Then, a mixture consisting of 15 parts of distilled water, 0.5 part of polyethylene glycol monooleyl ether (SOFTANOL-90, trademark for a product of Nippon Shokubai K.K.) and 4 parts of a perfume (No. 4744; a product of Hasegawa Koryo K.K.) was gradually added in about 30 minutes and the system emulsified in the same way as in Example 1. The resulting w/o emulsion was cast into a mold at about 80° C, and cooled to room temperature (20° C) by allowing to stand to form a pale yellow gel having a volume of 30 × 30 × 10 mm.

When this gel was allowed to stand at room temperature (20° C), it gave off the smell of the perfume even after 90 days. This means that the hydrous gel of this invention serves to control the rate of perfume release, and is useful as a controlled release material.

While the invention has been described in detail and with reference to specific embodiments thereof, it will be apparent to one skilled in the art that various changes and modifications can be made therein without departing from the spirit and scope thereof.

What is claimed is:

1. A hydrous gel consisting essentially of a heat-moldable w/o emulsion composed of about 15 to about 95% by weight of a continuous phase consisting of an A-B-A type teleblock copolymeric elastomer which consists of a hard polymer block A of vinyl compound and a soft polymer block B of a conjugated diene and an oil component and about 85 to about 5% by weight of a dispersed water phase resulting from the emulsification of water particles by an emulsifier having the property of forming a dispersed phase of innumerable emulsified water particles in the continuous phase consisting of the teleblock elastomer and the oil component and maintaining the form of the w/o emulsion in a stable fashion, said hydrous gel being capable of providing a gel product containing emulsified water particles stable at room temperature.

2. The hydrous gel of claim 1, wherein the hard polymer block A has a glass transition point of at least about 70° C and an average molecular weight of about 1,000 to about 100,000, and the soft polymer block B has a glass transition point of about −50° C to about 30° C and an average molecular weight of about 4,500 to about 1,000,000.

3. The hydrous gel of claim 1, wherein the oil component is selected from the group consisting of machine oils, cylinder oils, transformer oils, rosin oils and liquid paraffins.

4. The hydrous gel of claim 1, wherein the amount of the oil component is 100 parts by weight per about 5 to about 30 parts by weight of the teleblock elastomer.

5. The hydrous gel of claim 3, wherein the amount of the oil component is 100 parts by weight per about 5 to about 30 parts by weight of the teleblock elastomer.

6. The hydrous gel of claim 1, wherein a cross-linking agent for the teleblock elastomer is incorporated in an amount of about 0.01 to about 2 parts by weight per 100 parts by weight of the teleblock elastomer.

7. The hydrous gel of claim 1, wherein the emulsifier is a nonionic surface active agent.

8. The hydrous gel of claim 1, wherein the amount of the emulsifier is about 1 to about 20 parts by weight per 100 parts by weight of water.

9. The hydrous gel of claim 6, wherein the amount of the emulsifier is about 1 to about 20 parts by weight per 100 parts by weight of water.

10. The hydrous gel of claim 1, wherein the amount of the emulsifier is about 5 to about 10 parts by weight per 100 parts by weight of water.

11. The hydrous gel of claim 6, wherein the amount of the emulsifier is about 5 to about 10 parts by weight per 100 parts by weight of water.

12. A process for preparing a hydrous gel, which comprises dissolving an A-B-A teleblock copolymeric elastomer consisting of a hard polymer block A of a vinyl compound and a soft polymer block B of a conjugated diene in an excess of an oil component by heating, adding an emulsifier which has the property of forming a dispersed phase of innumerable emulsified water particles in the continuous phase consisting of the tele-block elastomer and the oil component and maintains the form of the w/o emulsion in a stable fashion and water to the resulting solution to disperse water therein and to form a w/o emulsion containing about 15 to about 95% by weight of a continuous phase consisting of the elastomer and the oil component and about 85 to about 5% by weight of an emulsified dispersed water phase, and then cooling the emulsion to room temperature.

13. The hydrous gel of claim 7, wherein the emulsifier is a nonionic surface active agent selected from the group consisting of polyethylene glycol monooleyl ether, polyethylene glycol mononyl phenyl ether, polyethylene glycol monododecyl phenyl ether and polyethylene glycol monolauryl ether.

14. The hydrous gel of claim 7, wherein the emulsifier is a nonionic surface active agent selected from the group consisting of sorbitan monolaurate, sorbitan monooleate, sorbitan sesquioleate, sorbitan monostearate and sorbitan monopalmitate.

15. The process of claim 12, wherein the hard polymer block A has a glass transition point of at least about 70° C and an average molecular weight of about 1,000 to about 100,000, and the soft polymer block B has a glass transition point of about −50° C to about 30° C and an average molecular weight of about 4,500 to about 1,000,000.

16. The process of claim 12, wherein the oil component is selected from the group consisting of machine oils, cylinder oils, transformer oils, rosin oils and liquid paraffins.

17. The process of claim 12, wherein the emulsifier is a nonionic surface active agent.

18. The process of claim 12, wherein the amount of the oil component is 100 parts by weight per about 5 to about 30 parts by weight of the teleblock elastomer.

19. The process of claim 12, wherein the amount of the emulsifier is about 1 to about 20 parts by weight per 100 parts by weight of water.

20. The process of claim 12, wherein the heating is a temperature of about 80° to about 170° C.

21. The hydrous gel of claim 1 wherein the hydrous gel is characterized by being easily deformed upon application of stress but substantially completely returns to its original state in about 1 to 2 minutes after removal of the stress.

22. The hydrous gel of claim 1 having a viscosity of 10 to about 500 poises at a temperature of 80° C or higher and being a non-flowable oily gel at room temperature to 50° C.

* * * * *